United States Patent [19]

Hernicz

[11] Patent Number: 4,717,504
[45] Date of Patent: Jan. 5, 1988

[54] REFLECTANCE STANDARD

[75] Inventor: Ralph S. Hernicz, Osceola, Ind.

[73] Assignee: Miles Inc., Elkhart, Ind.

[21] Appl. No.: 882,821

[22] Filed: Jul. 7, 1986

Related U.S. Application Data

[63] Continuation of Ser. No. 678,120, Dec. 4, 1984, abandoned.

[51] Int. Cl.[4] .................. G01N 31/00; G01N 33/00
[52] U.S. Cl. .................. 252/408.1; 524/423; 252/600
[58] Field of Search .............. 524/423; 252/408.1, 252/600

[56] References Cited

U.S. PATENT DOCUMENTS

| | | | |
|---|---|---|---|
| 3,405,088 | 10/1968 | Slocum | 524/423 |
| 3,773,708 | 11/1973 | Takahashi et al. | 524/423 X |
| 3,861,945 | 1/1975 | Hartzell et al. | 524/423 X |
| 3,933,875 | 1/1976 | Brose et al. | |
| 4,510,196 | 4/1985 | Carter, Jr. | 524/423 X |

Primary Examiner—John F. Terapane
Assistant Examiner—Susan Wolffe
Attorney, Agent, or Firm—Roger N. Coe

[57] ABSTRACT

Reflectance standards are prepared in accordance with the present invention by incorporating at least 40 percent by weight of barium sulphate into acrylate polymer such as methyl acrylate or methyl methacrylate. Thickness of the resulting polymer should be in excess of 0.25 centimeters. By incorporating varying percentages of carbon black in the mixture during mixing—various reflectance values can be obtained. The resulting reflectance standards can be utilized in the form of chips, plaques, sheets, or can be molded into various configurations, including that of an integrating sphere.

8 Claims, 2 Drawing Figures

REFLECTANCE STANDARD

This is a continuation of application Ser. No. 678,120 filed Dec. 4, 1984, now abandoned.

FIELD OF THE INVENTION

The present invention relates to a reflectance standard and, more particularly, this invention relates to a reflectance standard composed of barium sulphate and a methyl acrylate or methyl methacrylate polymer.

BACKGROUND OF THE INVENTION

Applications calling for the measurement of light reflectance, or the use of light reflectance measurements, are generally faced with a wide selection of materials which can be used for standardization of reflection measurements. A variety of powders, paints, plastics, tiles, etc. are used for the purpose of establishing a standard by which other reflectance measurements can be gauged. Unfortunately, materials which have good initial reflectance characteristics are often unstable to light, are fragile and lack durability, are not cleanable, are expensive, are difficult to work with or to manufacture, age poorly, fail to reflect a high percentage of incident light, lack uniform reflectance over a desired wavelength range, decrease substantially in reflectance at shorter wavelengths, etc. and thereby fail to have the characteristics necessary to achieve a good reflectance standard which is usable as a standard over long periods of time. Visible light is only a part of the electromagnetic energy band. All sources of light, whether natural sunlight or artificial light, emit energy in the ultraviolet and in the infrared bands, as well as visible energy in the form of light. Upon exposure to electromagnetic energy photochemical damage can take place. Normally such damage takes two forms; fading or darkening of colors and structural damage caused by the breakdown of molecular bonds. This damage is not instantaneous, but takes place over long periods of time and is the cumulative effect of exposure. Irradiation by visible light in the 400 to 500 nanometer range primarily causes fading or darkening of colors in materials selected as reference standards although some minor structural damage may also occur. Irradiation by ultraviolet energy in the 300 to 400 nanometer range can cause both structural damage, i.e., embrittlement, loss of tear strength, etc. and fading and darkening of colors. These problems are especially acute in those industries where reflectance standards or reflective coatings must be used for comparison purposes in various measuring and testing devices such as spectrophotometers, colorimeters, and reflectometers.

Examples of materials currently used for reflectance standard purposes which give rise to the problems mentioned above include pigmented paint, magnesium oxide, magnesium carbonate, Halon, and barium sulphate. Pigmented paint, for instance, can result in low reflectance, give rise to light stability problems, and can crack or chip upon aging. The use of magnesium oxide and magnesium carbonate presents problems of light stability, aging and efficiency. Barium sulphate and Halon powder are presently the most commonly used reflectance materials and form almost ideal white standards. Unfortunately, since barium sulphate and Halon exist as powders they are very fragile. Even when the powders are pressed, the barium sulphate and Halon remain fragile. Moreover, the pressed barium sulphate and Halon lack reproducible reflectance characteristics and they are not cleanable once the pressed or compacted surface is soiled.

SUMMARY OF THE INVENTION

An object of the present invention is to provide a material which can be used as a reflectance standard which is light stable and which has a high degree of reflectivity.

Another object of the present invention is to provide material which can be used as a reflectance standard in a variety of molded formats.

Still another object of the present invention is to provide a reflectance standard which does not have a large decrease in reflectance at lower wavelengths.

Yet another object of the present invention is to provide a reflectance standard which is cleanable and easy to manufacture.

In accordance with the present invention, at least 40 percent by weight of barium sulphate is incorporated into a methyl acrylate or methyl methacrylate polymer, i.e., an "acrylate polymer", for use as a reflectance standard. It has been found that the thickness of the resulting polymer should be in excess of about 0.25 centimeters. Carbon black can be added in different proportions to obtain reflectance standards having different reflectance values. The resulting reflectance standards can be utilized in the form of chips, sheets or can be molded into various configurations, including that of an integrating sphere.

BRIEF DESCRIPTION OF THE DRAWINGS

Other and further objects, advantages and features of the invention will be apparent to those skilled in the art from the following detailed description thereof, taken in conjunction with accompanying drawings in which.

DETAILED DESCRIPTION OF THE INVENTION

Figure 1:
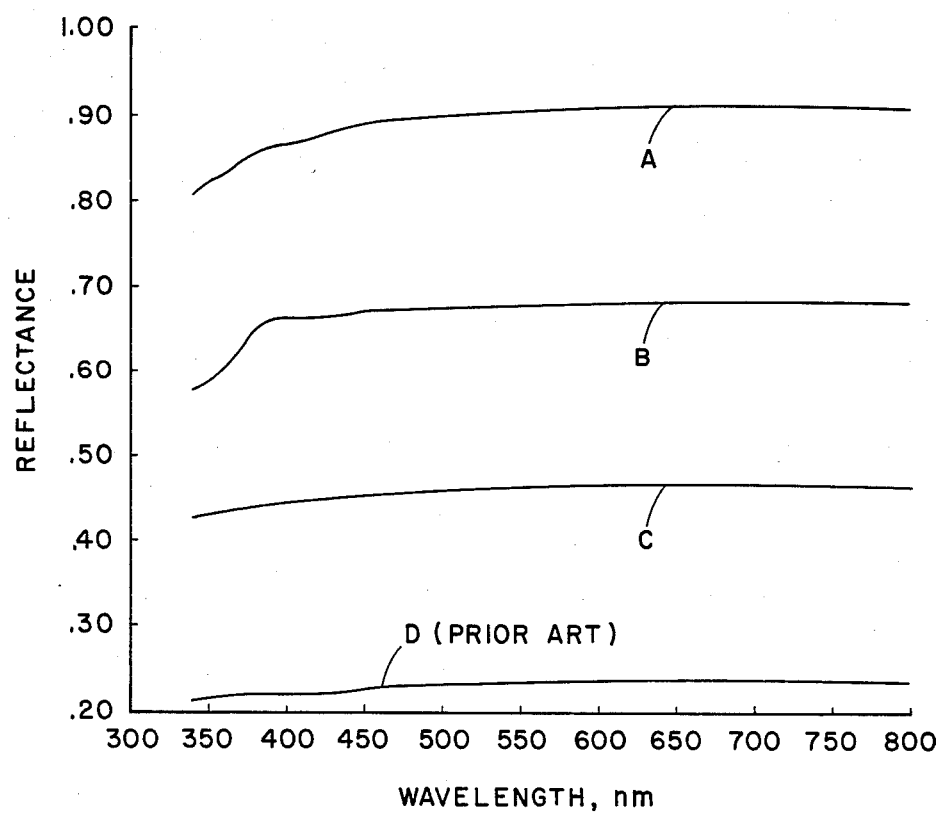
FIG. 1 is a plot of wavelength vs. reflectance for various reflectance standards prepared in accordance with the present invention as well as a prior art black reflectance standard obtained from the National Bureau of Standards.

As indicated above, the reflectance standards of the present invention are prepared by incorporating barium sulphate in excess of 40 weight percent into thermoplastic methyl acrylate or methyl methacrylate polymers such as Plexiglas, which is the trademark of Rohm & Haas Co., Philadelphia, Pennsylvania. Ultraviolet filtering formulations of Plexiglas are sold by Rohm and Haas Company as Plexiglas UVA 3-7 molding pellets. Methyl acrylate and methyl methacrylate polymers are ideal for this purpose since the resulting plastic is transparent over wavelengths of interest. Preferred methyl acrylate and methyl methacrylate polymeric materials for use in the present invention are V811-UVT and V920-UVT-100 Plexiglas obtained from the RTP Company of Winona, Minn. which have a transmittance in excess of 90% from 325 nm to 1000 nm for a 0.32 cm thick sample. The advantage of using special formulations of Plexiglas acrylic plastic in which most or all ultraviolet energy is filtered out is that such materials offer protection from structural damage caused by irradiation of ultraviolet energy below 400 nanometers. Typically, the acrylic plastic is available as molding pellets which is a convenient form for combination with the barium sulphate as described herein.

In contrast, when other materials, such as polystyrene, ethylene and propylene polymers, nylon, polycarbonate, etc. were substituted for methyl acrylate and methyl methacrylate polymers the resulting material could not be used because the plastics lacked sufficient transmittance characteristics over the wavelength range of interest. Most plastics have an absorption band around 400 nanometers (nm) which makes them unsuitable for use as reference standards.

The barium sulphate incorporated into the methyl methacrylate and methyl acrylate polymeric materials in accordance with the present invention must be of U.S.P. grade and a particle size of from 0.3 $\mu$m to 2 $\mu$m (microns). For optimum performance, the particles should be spherical to oblong in shape and have an average particle size of 0.75$\times$0.50 $\mu$m.

It has been found that the amount of barium sulphate incorporated into the methyl acrylate or methyl methacrylate polymeric material should be in excess of 40 weight percent. This is far in excess of the percentage of barium sulphate which has been used in the past for incorporation into plastic materials as a filler. Typically, the amount of barium sulphate used as a filler is less than five weight percent.

Methods of polymerizing the acrylate and methacrylate esters to form polymeric materials are well known. Thus, for purposes of this invention, the polymers herein can be made by conventional polymerization procedures from the monomeric materials. Basically, these procedures comprise heating the monomers for a sufficient period of time to obtain the resulting polymer. Preferably, the barium sulphate powder is mixed with granules of the thermoplastic methyl acrylate or methyl methacrylate polymeric material and the mixture is heated until a homogeneous mixture is obtained. Conveniently, the mixing can occur using an extruder. The extruded material is pelletized and then formed into the desired shape or configuration before being allowed to cool. Once the composition has cooled a hard, durable and cleanable reference standard is achieved. Thus, the resulting reference standard is not fragile and if it becomes dirty after use one can simply wash the plastic material to obtain a clean surface. If desired, the reference standard can have a smooth surface or a textured surface, depending on the particular application.

The resulting reflectance standard can achieve a reflectance of about 90 percent or more of the incident light having wavelengths between 3400 and 8000 angstrom units. This level of reflectance is usually considered in the art as a useful level of white light reflectancy since it is sufficiently "white" to be considered a white light reflectance standard.

Other reflectance standards can be prepared by incorporating carbon black to decrease the amount of reflectance over the desired wavelength range. The carbon black should be of U.S.P. grade. The amount of carbon black which can be added generally ranges from 0 to 0.05 weight percent. While theoretically there is no upper limit on the amount of carbon black which can be added normally one would not need to add in excess of 0.02 weight percent of carbon black since a satisfactory black reflectance standard can be obtained from the National Bureau of Standards.

Normally, other additives such as plasticizers, fillers, extenders, etc. are not necessary and indeed should not be added to the plastic composition during the formation of the reference standards since additives can tend to cause UV absorption.

The following examples are illustrative of the above described invention and should not be constructed as a limitation thereon.

EXAMPLE I

Sixty weight percent of barium sulphate (USP grade, 325 mesh) is added to V920-UVT-100 Plexiglas obtained from the RTP Company by of Winona, Minn. mixing the barium sulphate with the Plexiglas material while heating the granules of the polymeric material until a homogeneous mixture is obtained. The mixture is molded in the form of a 3 inch by 4 inch plaque having a thickness of 0.32 cm.

The resulting material has a reflectance sufficient to be useful as a white light reflectance standard. The reflectance of the resulting plate as determined using a Cary-17 spectrophotometer was plotted against wavelength in FIG. 1 as line A.

Figure 2:
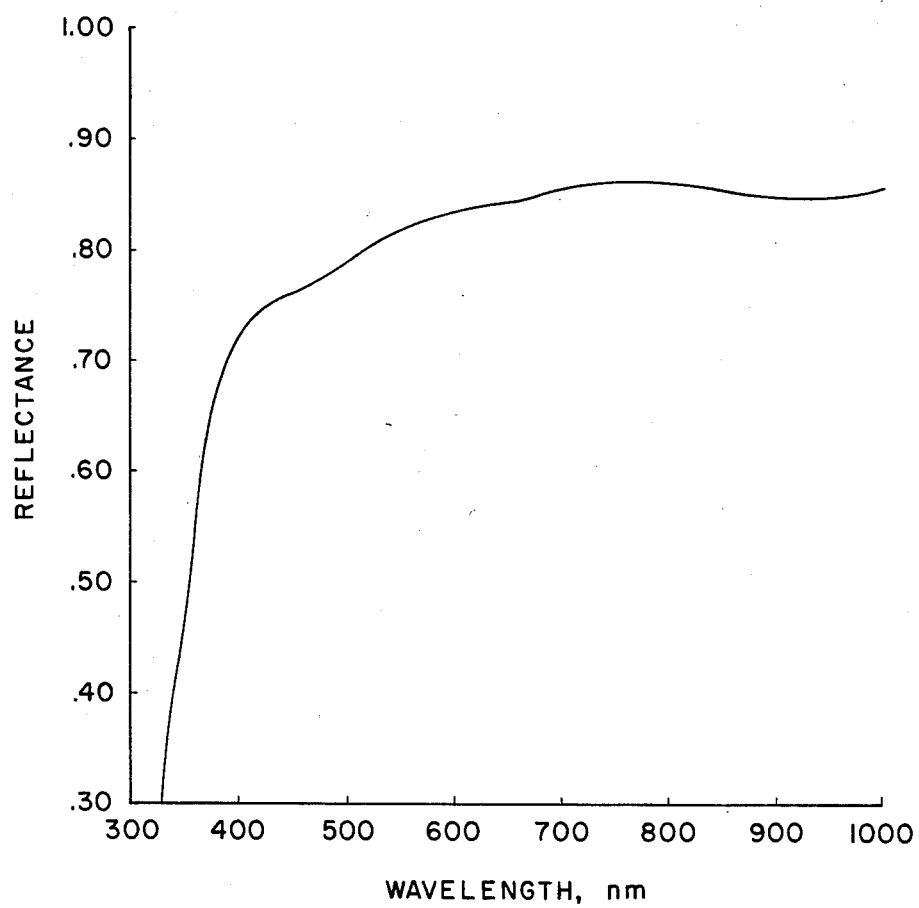
FIG. 2 is a plot of wavelength vs. reflectance for a prior art white ceramic tile reference standard of the National Bureau of Standards illustrating a large decrease in reflectance at lower wavelengths.

The reflectance standard of this Example should be compared with a prior art white ceramic tile reflectance standard, Standard Reference Material 2019, supplied by the National Bureau of Standards which is plotted in FIG. 2 to show reflectance over a similar wavelength range. It will be observed that in contrast to the reference standard of the present invention the National Bureau of Standards ceramic tile reference standard has a reflectance of approximately 85 percent over the wavelength range of 700 to a 1000 and this significantly falls off at lower wavelengths. This substantial reduction did not occur with the reflectance standards of the present invention.

EXAMPLE II

Varying percentages of carbon black powder (Monarch 880, Cabot furnace carbon black) are added to the compositions used to prepare reflectance standard in accordance with Example I. Specifically, 0.00044 weight percent of carbon black is added in one embodiment to the barium sulphate polymeric mixture described in Example I and 0.01762 weight percent of carbon black was added in another instance. The procedure for incorporating the materials to form reference standards is exactly the same as in Example I.

By incorporating the carbon black in the percentages indicated above varying shades of gray were achieved which is illustrated in FIG. 1. Line B illustrates the reference standard obtained by incorporating 0.00044 weight percent of carbon black whereas line C illustrates the reflectance standard achieved by incorporating 0.01762 weight percent of carbon black. It can be seen from the plot of reflectance vs. wavelength for the resulting reflectance standards that lines B and C do not decrease significantly at the shorter wavelengths.

For comparison purposes, line D in FIG. 1 is a plot of reflectance vs. wavelength for a black reflectance standard, Standard Reference Material 2021, of the National Bureau of Standards.

Obviously, by incorporating various percentages of carbon black one can achieve an infinite number of reflectance standards ranging between a white reference standard such as that illustrated by line A in FIG. 1 and a black reference standard similar to that illustrated in line D of FIG. 1. For many applications it is desirable to utilize such reflectance standards which are between the extremes of a white reflectance standard and a black reflectance standard.

The material used to form reflectance standards in accordance with the present invention can be molded into almost any desired configuration, even including the shape of an integrating sphere.

Other "white" materials added to plastic suffer from serious flaws. For example, Telfon becomes transparent under normal molding condition. Magnesium oxide and magnesium carbonate degrade under UV light. Titanium dioxide has an absorption band around 400 nm and thereby has a low reflectance in the UV.

From the the foregoing, it will be seen that this invention is well adapted to attain all of the ends and objects herein before set forth together with other advantages which are obvious and inherent. The materials used in accordance with the present invention are capable of providing a white reflectance standard or gray reflectance standards which do not show a large decrease in reflectance at wavelengths in the range of 340 to 800 nanometers. Moreover, the reflectance standards have the advantage of being durable and readily cleanable. The reflectance standards are easy to manufacture and can be formed into many desired configurations suitable for use in a wide variety of reflectance measuring instrumentation. In addition, the standards can be utilized over wavelengths in which most plastics have an absorption band rendering them unsuitable for use as standards.

Another advantage of the reference standards prepared in accordance with the present invention is the fact that reference standards can be used over long periods of time without reduction in reflectancy characteristics with age. Moreover, the reflectance standards can be used with essentially any desired light source such as incandescent, LED, arc lamps and flash lamps.

Obviously, many modifications and variations of the invention as hereinbefore set forth can be made without departing from the spirit and scope thereof and therefore only such limitations should be imposed as are indicated by the appended claims.

What is claimed is:

1. A method for standardizing of light reflection measurements consisting essentially of directing light on a reflectance standard comprising an acrylate polymer having transmittance greater than 90% over the range of from 325 nanometers to 1000 nanometers for a 0.32 centimeter thick sample and at least 40% by weight of barium sulphate, wherein said barium sulphate has a purity equivalent to at least USP Grade and a particle size of between about 0.3 to about 2 microns, and measuring the light reflected from said reflective standard.

2. The method for standardization of light reflection measurements in claim 1 in which the barium sulphate has an average particle size of 0.75 by 0.5 micron.

3. The method for standardization of light reflection measurements of claim 1 in which the acrylate polymer is methylacrylate polymer.

4. The method for standardization of light reflection measurements of claim 1 in which the acrylate polymer is a methylmethacrylate polymer.

5. The method for standardization of light reflection measurments of claim 1 which also includes up 0.05 weight percent carbon black in the reflectance standard.

6. The method of standardization of light reflection measurements of claim 1 in which the barium sulphate is present in an excess of 60 weight percent.

7. The method of standardization of light reflection measurements of claim 1 in which the particles of barium sulphate are spherical to oblong in shape.

8. The method for standardization of light reflection measurements of claim 1 in which the measurements are made at wavelengths in the range of 340 to 800 nanometers.

* * * * *